(12) United States Patent
Johansson

(10) Patent No.: US 6,613,884 B1
(45) Date of Patent: Sep. 2, 2003

(54) METHOD FOR THE REMOVAL/PURIFICATION OF SERUM ALBUMINS AND MEANS FOR USE IN THE METHOD

(75) Inventor: Hans Johansson, Summit, NJ (US)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/719,511

(22) PCT Filed: May 25, 1999

(86) PCT No.: PCT/SE99/00879

§ 371 (c)(1),
(2), (4) Date: Feb. 15, 2001

(87) PCT Pub. No.: WO99/65943

PCT Pub. Date: Dec. 23, 1999

(30) Foreign Application Priority Data

Jun. 18, 1998 (SE) ............................................. 9802213

(51) Int. Cl.⁷ .......................... C07K 1/00; C07K 14/00; C07K 16/00; C07K 17/00; A23J 1/00
(52) U.S. Cl. ....................... 530/364; 530/412; 530/350; 530/362; 530/363; 530/413
(58) Field of Search ................................. 435/455, 463, 435/320.1, 325; 800/18, 21, 22, 25, 3; 530/364, 412, 350, 362, 363, 413

(56) References Cited

U.S. PATENT DOCUMENTS 5,648,243 A * 7/1997 Hurwitz et al. ............ 435/69.6
5,741,957 A * 4/1998 Deboer et al. ................ 800/2

OTHER PUBLICATIONS

Sjobring et. al.; Isolation and characterization of a 14–kDa albumin–binding fragment of streptococcal protein G, 1988, The Journal of Immunology vol. 140, Issue5: 1595–1599.*
Kraulis et. al.; The serum albumin–binding domain of streptoccal protein G is a three–helical bundle: a heteronuclear NMR study, 1996, FEBS Letters 378: 190–194.*
Cuatrocasas et. al.; 1970, Affinity Chromatograpy: 370–375.*

* cited by examiner

Primary Examiner—Deborah Crouch
Assistant Examiner—Thai-An N. Ton
(74) Attorney, Agent, or Firm—Stephen G. Ryan; Royal N. Ronning, Jr.

(57) ABSTRACT

A method for removing a serum albumin from a mixture of other compounds by contacting said mixture with a ligand a) having affinity for and enabling selective binding of the serum albumin and b) being attached to a base matrix insoluble in the aqueous media used or being possible to attach to such a matrix after having become bound to the serum albumin, characterized in that said ligand is derived from an albumin binding bacterial cell surface receptor and that the ligand lacks the IgG-binding and/or $\alpha_2$-macroglobulin-binding ability found in native forms of these type of bacterial receptors. An albumin-binding ligand derived from a cell surface bacterial receptor and attached covalently to a carrier matrix, characterized in that the ligand is monovalent with respect to ability to bind a serum albumin. A method for removal of serum albumin from a sample that is to be assayed for non-serum albumin components. The characteristic feature is to subject the sample to affinity adsorption by an albumin-binding ligand derived from an albumin-binding receptor.

8 Claims, No Drawings

METHOD FOR THE REMOVAL/PURIFICATION OF SERUM ALBUMINS AND MEANS FOR USE IN THE METHOD

BACKGROUND OF THE INVENTION

1. Field of the Invention

The present invention concerns a method for the separation/removal of a mammalian serum albumin from a solution containing a mixture of proteins in order to obtain a solution/preparation that is substantially devoid of the serum albumin. The invention also concerns novel immobilized forms of albumin-binding ligands deriving from native forms of bacterial receptors that are able to bind to one or more serum albumins.

2. Technical Background

For a long time there has been a large demand for mammalian serum albumins, for instance serum albumin of human or bovine origin (HSA and BSA, respectively). For HSA this has mainly depended on its therapeutic use as a plasma volume expander. Originally serum albumins were obtained from sera/plasma of the appropriate species origin. For some years the focus has been to produce serum albumins recombinantly, in particular HSA. For bacterially produced recombinant forms, it has become urgent to remove host cell contaminants because they may be hazardous in vivo to mammals. For some time it has become apparent that producing HSA in transgenic animals should be beneficial, for instance in transgenic cows. This latter alternative, however, has the drawback that HSA will be present in mixture with the HSA analogue of the host animal (for instance with BSA if HSA produced in cows). This has created novel purification problems, for instance the specific removal of BSA from HSA.

Serum albumin preparations intended for use in vivo shall according to accepted practice contain<0,01%, such as<0,001% proteins that are heterologous to the species to which the preparation is to be administered. HSA preparations, for instance, that are to be used in humans shall contain<0,01%, such as<0,001% BSA. All percentages are w/w.

Removal of serum albumins has also been a concern when assaying samples containing serum albumin for other components. Blood derived samples such as whole blood, serum and plasma are typical examples. In this kind of samples serum albumin is one of most abundant substances and may disturb assays for other substances that are present in lower amounts. In analyzing protein components after, for instance, two-dimensional gel electrophoresis or mass spectrometric fragmentation, serum albumin will easily disturb.

Various forms of affinity chromatography and/or ion exchange chromatography have earlier been applied to the purification of serum albumins. For affinity chromatography the general goal has been to find a chromatographic media (ligand attached to a chromatographic base matrix) that provide the sufficient specificity in order to remove either predetermined contaminants or the serum albumin desired as the end product from complex mixtures.

3. Description of Related Art

Illustrative examples of ligands previously used and having selectivity for serum albumins are given by Theodore Peters in All about Albumin-Biochemistry, Genetics and Medical Applications, (Ed. Theodore Peters, Jr., Academic Press (1996) pages 77–126. There are also known other compounds that bind serum albumins, even with species selectivity, that for various reasons have not found use in the selective/specific removal and/or purification of serum albumins. Examples are albumin binding receptors (proteins) present on the cell surface of certain bacteria, typically streptococci. See for instance Nygren et al., Eur. J. Biochem. 193 (1990) 143–148 (Protein G), Guss et al., WO 9507300 (Protein MAG), Jonsson et al., Infect. Immun. 63 (1955) 2968–2975 (Protein ZAG). These bacterial receptors frequently also bind to other proteins, for instance Protein G to IgG and Protein MAG and ZAG to IgG and $\alpha_2$-macroglobulin. The various extra binding abilities of these proteins make them less suitable as ligands for the selective/specific removal of serum albumin from complex protein mixtures. The main use of their albumin-binding fragments has been as fusion partners, for instance in order to have an affinity handle attached to a protein to be purified. To the extent that immobilised forms have been produced it has been in order to make binding studies in relation to serum albumins from various mammalian species. See further Nygren et al (Eur. J. Biochem. 193 (1990) 143–148). Guss et al (WO 9507300) has outlined in a patent example to use intact protein MAG in an attempt to roughly purify albumin from mammalian blood. However it is apparent from Guss et al's results that also IgG and $\alpha_2$-macroglobulin were bound together with albumin.

Additional examples of known bacterial receptors binding to serum albumin are Protein H and M proteins, both from streptococci.

Native forms of this kind of receptors typically have more than one subsequence that is responsible for binding to albumin or IgG. The receptors may contain 1, 2 or 3 albumin-binding and/or IgG-binding regions. Functionally similar regions may differ in sequence.

BRIEF SUMMARY OF THE INVENTION

Objectives of the Invention

The first objective of the invention is to provide improved affinity methods for the removal of a serum albumin from a mixture of proteins in order to produce the serum albumin in pure form or a preparation essentially free of the removed serum albumin.

A second objective is to provide an affinity method as defined above which has an improved selectivity for a certain serum albumin that exists in mixture with one or more other serum albumins.

A third objective is to provide new affinity matrices carrying albumin-binding ligands having improved selectivities for serum albumins.

A fourth objective is an improved method for removal of serum albumin in samples that are to be assayed for one or more non-serum albumin components.

The methods for removal of serum albumin are based on matrices that carry an albumin binding ligand.

The Invention

It has now surprisingly been found that the albumin binding capacity of the type of bacterial cell surface receptors mentioned above may advantageously be utilized for the selective removal and/or purification of serum albumins.

The inventive method encompasses that a mixture which contains (a) a serum albumin that is derived for a certain mammalian species and (b) other compounds, in particular proteins, is contacted with a ligand under conditions permitting binding (adsorption) of the serum albumin to the ligand. The ligand is preselected to have affinity for the serum albumin and is attached to a base matrix or is possible to attach to a base matrix after having become bound to the serum albumin. The invention has the characterizing feature that the ligand derives from an albumin-binding form of a bacterial receptor having affinity for a serum albumin, said form not encompassing the IgG- or $\alpha_2$-macroglobulin-binding ability of native forms of these kind of receptors. The form is typically a fragment not encompassing the amino acid subsequences responsible for ability to bind to IgG- and/or $\alpha$2-macroglobulin.

DETAILED DESCRIPTION OF THE INVENTION

The Ligand

It is previously known that albumin-binding fragments can be obtained from the above-mentioned bacterial cell surface receptors, e.g. proteins G, MAG and ZAG and protein H and M-proteins. With present knowledge the most preferred fragments to be used as ligands are monovalent with respect to albumin binding, e.g. forms of the native receptor in which all except one of the albumin binding regions have been neutralized. This does not exclude that also divalent, trivalent and other polyvalent fragments can be used as long as other disturbing binding abilities are not present. By recombinant techniques it is in principle possible to link any number of albumin binding regions to each other in series.

In streptococcal protein G (SPG) the various regions are arranged as described for strain G148. See for instance FIG. 1 in Sjölander et al., J. Immunol. Meth. 201 (1997) 115–123 which is based on Nygren et al., J. Mol. Recognit. 1 (1988) 69-:

| | | alb1 | | alb2 | | alb3 | | | | | | | |
|---|---|---|---|---|---|---|---|---|---|---|---|---|---|
| Ss | E | A1 | B1 | A2 | B2 | A3 | S | C1 | D1 | C2 | D2 | C3 | W |
| | | serum albumin binding | | | | | | IgG binding | | | | | |

Alb1, alb2 and alb3 correspond to the three albumin binding regions of SPG from strain G148. The number of albumin-binding regions may differ between strains.

In addition to pure fragments various recombinant constructs derived from the native forms and their albumin binding fragments can also be used. Illustrative examples are mutated forms that retain their albumin binding capacity but lacks the ability to bind to IgG and/or $\alpha_2$-macroglobulin, and forms in which there have been added or inserted one or more amino acids, for instance cysteine, that facilitate covalent attachment to a carrier matrix. Addition/insertion of amino acid residues preferably takes place outside an albumin-binding site, for instance at the carboxy and/or amino terminal end. In case the change is within an albumin-binding site and the binding ability of the site is to be retained the replacing amino acid residue should be conserved in relation to the replaced residue.

The Sample Containing the Serum Albumin to be Removed/purified

The serum albumin to be removed and/or purified typically exists in mixture with other proteins and/or biomolecules. The sample may be (a) blood preparations (such as plasma and serum), (b) fermentation liquids obtained from cultured host cells that have been transformed to express a serum albumin, (c) biological fluids obtained from transgenic mammals transformed to produce a serum albumin of another species, (d) and working up preparations derived from anyone of these types of liquids, etc. In case of liquids derived from transgeneic animals the liquids will often contain also the normal serum albumin of the species concerned.

The Matrix and the Attachment of the Ligand Thereto

In the preferred modes of the invention the ligand is attached to a base matrix that is insoluble in the aqueous media used. Such matrices often are based on polymers that expose a hydrophilic surface to the aqueous media used, i.e. expose hydroxy (—OH), carboxy (—COOH), carboxamido (—$CONH_2$, possibly in N- substituted forms), amino (—$NH_2$, possibly in substituted form), oligo- or polyethylenoxy groups on their external and, if present, also on internal surfaces. Typically the matrices are of the same kind as those normally used as chromatographic matrices. The polymers may, for instance, be based on polysaccharides, such as dextran, starch, cellulose, pullulan, agarose etc, which if necessary have been crosslinked, for instance with bisepoxides, epihalohydrins, 1,2,3-trihalo substituted lower hydrocarbons, to provide a suitable porosity and rigidity. The matrices may also be based on synthetic polymers, such as polyvinyl alcohol, poly hydroxyalkyl acrylates, poly hydroxyalkyl methacrylates, poly acrylamides, polymethacrylamides etc. In case of hydrophobic polymers, such as those based on divinyl and monovinyl substituted benzenes, the surfaces of the matrices are often hydrophilized to expose hydrophilic groups as defined above to a surrounding aqueous liquid.

The matrices may also be of inorganic nature, e.g. silica, zirkonium oxide etc.

Physically the insoluble matrices may be in the form of porous monoliths or in beaded/particle form that can be porous or non-porous. Matrices in beaded/particle form can be used as a packed bed or in a suspended form. Suspended forms include so called classified expanded beds and pure suspensions in which the particles/beads are moving round completely. In case of monoliths, packed bed and classified expanded beds, the separation procedure may be classified as a normal chromatography with a concentration gradient of adsorbed molecules being established along the flow direction. In case of pure suspension the separation procedure will be in the batch wise mode.

For suspensions, the beads/particles may contain a densifying filler material that will permit increased flow rates in case of classified expanded beds and facilitate sedimentation of the beads/particles after affinty binding (adsorbtion). See for instance WO-A-9717132 (Amersham Pharmacia Biotech AB) and WO-A-9200799 (Upfront Chromatography).

The ligand may be attached to the matrices via conventional coupling techniques utilising, e.g. amino and/or carboxy groups present in the ligand. In case a cysteine residue is present it may be utilized as well (thioether or disulfide attachments). Bisepoxides, epichlorohydrin, CNBr, N-hydroxysuccinimide (NHS) etc are typical coupling reagents.

Between the base matrix and the ligand there is often introduced a spacer that will improve the availability of the ligand and facilitate the chemical coupling of the ligand to the matrix. Generally the spacer provides a hydrocarbon chain that has a length between 1–50 atoms. The hydrocarbon chain may be straight, branched or cyclic and optionally interrupted by one or more ether oxygen or amino nitrogen atoms and/or optionally substituted with one or more hydroxy, lower alkoxy, or amino group (—$NH_2/NH_3^+$, where each hydrogen may be replaced with a lower alkyl or a lower acyl group). By lower alkyl or acyl group is primarily intended C1–C10 alkyls/acyls. The spacer group may also, depending to coupling methodology, comprise ester, amido, thioether, etc groups that have the sufficient hydrolytic stability.

The spacer may also be polymeric providing attachments of several ligands per spacer. This type of spacers is often hydrophilic and called extenders, tentacles etc. See for instance International Patent Application PCT/SE98/00189 (Amersham Pharmacia Biotech AB).

It can be envisaged that the ligand may also be attached to the matrix by non-covalent bonding, such as physical adsorption or biospecific adsorption. For the latter type of binding the biotin-strepavidin system may be utilized.

As a potential alternative the ligand may be in soluble form that subsequent to binding to a serum albumin is insolubilized. This may be accomplished, for instance, by having the ligand conjugated to biotin and insolubilizing by contacting the formed complex between the serum albumin and the soluble ligand-biotin conjugate with a strepavidin-matrix.

Procedural Steps

During the adsorption step the conditions are selected so as to promote binding between the ligand and the serum albumin intended. pH is typically selected between 4–8, the ionic strength in the interval corresponding to 0–3 M NaCl, and the temperature in the interval 0–40° C., with preference for 4–37° C. The exact values will depend on the species origin of the serum albumin to be removed/purified and of the ligand attached to the matrix.

After adsorption the serum albumin bound to the ligand may be further worked up, for instance by first desorbing the bound serum albumin and subsequently subjecting it to further adsorption steps, for instance on an ion exchanger. Suitably desorption conditions may include change of pH, ionic strength, temperature and or addition of compounds interfering with binding. The main rules should then of course be not to change the conditions so that the serum albumin becomes irreversibly denatured.

Binding of the serum albumin to the ligand may be preceded by other adsorption steps. Such steps may for instance be based on ion exchange or on immune ligands.

In case the starting mixtures contains two serum albumins, one of which is adsorbed to the ligand and the other retained in the liquid, working up can continue on the liquid in order purify the serum albumin retained in the liquid.

In case the serum albumin has been removed in order to prepare samples low in serum albumin for assaying purposes, the sample is afterwards assayed, optionally after one or more additional conditioning steps. See above. One separate aspect of the invention is an albumin-binding ligand derived from a cell surface bacterial receptor and attached covalently to a carrier matrix. This aspect is characterized in that the ligand is monovalent with respect to ability to bind a serum albumin. In the most preferred mode at the priority date the ligand essentially corresponds to region A3 of SPG. See above. One further inventive aspect is to use anyone of the above-mentioned bacterial receptors and/or their albumin-binding modifications or fragments for the removal of serum albumin from a biological sample to be assayed for at least one other component that is not serum albumin. By including also the IgG-binding and/or $\alpha_2$-macroglobulin subsequences of the receptors also IgG and/or $\alpha_2$-macroglobulin will be removed. The selection of matrix, coupling technology, conditions for the binding step etc are essentially the same as described above. After removal of serum albumin, possibly in combination with removal of IgG and/or $\alpha_2$-macroglobulin and, if so desired, one or more additional conditioning steps, the sample is subjected to the assay contemplated. Typically assays involve 2-dimensional gel electrophoresis and/or mass spectrometric fragmentation and final analyses of the individual proteins and/or their fragmentation patterns. In principle any protein can be assayed after the pretreatment described above. Exceptions are serum albumin, and depending upon ligand also IgG and/or $\alpha2$-macroglobulin.

The invention is further defined in the appended claims and will now be further described by experimental support regarding the most preferred fragment.

EXPERIMENTAL PART

Immobilisation: The protein used in this study was a 7.1 kDa fragment of Streptococcal protein G containing the complete albumin binding domain, A3 (fragment SPG-ABD3, aa 254–299 in Kraulis et al., FEBS.letter 378 (1996) 190–194). Approximately 2 mg of the fragment was immobilised on a 1 ml NHS-activated column, HiTrap, according to the manufacturers instruction (Amersham Pharmacia Biotech AB, Uppsala, Sweden) (NHS=N-hydroxy-succinimide).

Chromatography conditions: All samples were adjusted to pH 7.0 before loading onto the column. A buffer consisting of 20 mM sodium phosphate and 150 mM sodium chloride, pH 7.0, was used for equilibration and washing after sample loading on the column (Buffer A).

Elution was performed by decreasing pH to 2.7 by applying a 20 mM citrate, 150 mM sodium chloride buffer, pH 2.7 (Buffer B).

Samples: Human serum albumin HSA (Sigma, St Louis, Mo, U.S.A.) 2 mg/ml in Buffer A, bovine serum albumin BSA (Sigma, St Louis, Mo, U.S.A.) 2 mg/ml in Buffer A and acid treated bovine whey, plain or spiked with BSA or HSA. All samples was adjusted to pH 7.0 and filtered by a 45 $\mu$l depth filter prior to application.

Chromatographic procedure: The column was equilibrated with approximately 5 column volumes (Cv) of Buffer A. Subsequently 2 ml of sample was applied and the column was further washed with another 6 Cv of buffer A before elution was performed by applying 5 Cv of Buffer B. The procedure was followed by on-line UV detection at 280 nm. UV-adsorbing material passing through the column unhindered or eluted with buffer B was collected and further analysed by SDS-PAGE and silver staining for detection of proteins.

Results: When HSA was present in the sample, HSA was quantitatively bound to the column and subsequently eluted by Buffer B. When BSA was present in the sample, BSA was detected in the break through and no BSA could be detected in the eluate. In the case of plain bovine whey all proteins detected in the sample by SDS-PAGE/silver staining could also be detected in the breakthrough while no proteins at all could be detected in the eluate. The results show that a fragment of an albumin binding bacterial cell surface receptor may have an extremely high selectivity for adsorbing HSA from mixtures containing both HSA and BSA.

What is claimed is:

1. A method for separating human serum albumin from a mixture including a human serum albumin analogue, said method comprising:

a) contacting a mixture containing human serum albumin and a human serum albumin analogue with a ligand wherein said ligand:

i) is derived from a fragment of streptococcal protein G comprising the complete A3 albumin binding domain, said fragment further lacks IgG-binding ability or $\alpha_2$-macroglobulin-binding ability, or both; and ii) is directly or indirectly attached to a base matrix insoluble in aqueous media; or iii) is attached to a base matrix insoluble in aqueous media after formation of a human serum albumin-ligand complex;

b) binding said human serum albumin to said ligand to form a complex; and c) separating said human serum albumin from the mixture comprising said human serum albumin analogue.

2. The method of claim 1, wherein said ligand contains one or more individual subunits that bind to serum albumin.

3. The method of claim 2, wherein said ligand contains only one serum albumin binding subunit.

4. The method of claim 1, wherein said mixture derives from a host that expresses human serum albumin as a heterologous protein.

5. The method of claim 1, wherein said ligand is covalently attached to said matrix.

6. The method of claim 5, wherein said ligand is covalently attached via one or more groups selected from the group consisting of: an amino group, a carboxy group and a mercapto group, present in an amino acid of the ligand.

7. The method of claim 1, further comprising eluting said human serum albumin from said base matrix and optionally, further processing it.

8. A method for separating human serum albumin, IgG and $\alpha_2$-macroglobulin from a mixture comprising a human serum albumin analogue, said method comprising:

a) contacting a mixture comprising human serum albumin and a human serum albumin analogue with a ligand, wherein said ligand:
   i) is derived from a fragment of streptococcal protein G and comprises the complete A3 albumin binding domain; and
   ii) is directly or indirectly attached to a base matrix insoluble in aqueous media; or
   iii) is attached to a base matrix insoluble in aqueous media after formation of a human serum albumin-IgG-$\alpha_2$-macroglobulin-ligand complex;
b) binding said human serum albumin, IgG and $\alpha_2$-macroglobulin with said ligand to form a complex; and
c) separating said human serum albumin, IgG and $\alpha_2$-macroglobulin from the mixture comprising said human serum albumin analogue.

* * * * *